United States Patent
Cronin et al.

(10) Patent No.: US 10,464,798 B2
(45) Date of Patent: Nov. 5, 2019

(54) RECOMMENDING MODIFICATION FOR POD-BASED BEVERAGES

(71) Applicant: Jooster IP AG, Bielbenken BL (CH)

(72) Inventors: John Cronin, Bonita Springs, FL (US); Seth Melvin Cronin, Essex Junction, VT (US)

(73) Assignee: Jooster IP AG, BielBenken BL (CH)

( * ) Notice: Subject to any disclaimer, the term of this patent is extended or adjusted under 35 U.S.C. 154(b) by 0 days.

(21) Appl. No.: 16/105,681

(22) Filed: Aug. 20, 2018

(65) Prior Publication Data
US 2018/0352836 A1 Dec. 13, 2018

Related U.S. Application Data

(63) Continuation of application No. PCT/US2017/018501, filed on Feb. 17, 2017.
(Continued)

(51) Int. Cl.
*A61B 5/00* (2006.01)
*B67D 1/00* (2006.01)
(Continued)

(52) U.S. Cl.
CPC .............. *B67D 1/0078* (2013.01); *A23L 2/12* (2013.01); *A47J 31/005* (2013.01); *A47J 31/401* (2013.01); *A47J 31/404* (2013.01); *A47J 31/407* (2013.01); *A47J 31/4407* (2013.01); *A47J 31/521* (2018.08); *A47J 31/525* (2018.08); *A61B 5/1118* (2013.01); *A61B 5/162* (2013.01); *A61B 5/4815* (2013.01); *A61B 5/4866* (2013.01); *A63B 24/0062* (2013.01); *B65D 25/08* (2013.01); *B65D 51/2807* (2013.01); *B65D 85/8043* (2013.01); *B65D 85/8046* (2013.01); *B67D 1/00* (2013.01); *B67D 1/0042* (2013.01); *G06F 3/0482* (2013.01);
(Continued)

(58) Field of Classification Search
CPC ...... G06F 19/3475; G07F 13/065; A23G 9/42
See application file for complete search history.

(56) References Cited

U.S. PATENT DOCUMENTS 8,985,395 B2 * 3/2015 Tansey ................ A47J 31/44
222/102
9,173,517 B2 * 11/2015 Bulgin ................ A47J 31/401
(Continued)

FOREIGN PATENT DOCUMENTS

WO 2017143282 A1 8/2017

OTHER PUBLICATIONS

Korean Intellectual Property Office, International Search Report for PCT Application No. PCT/US2017/018501, dated Apr. 26, 2017.
(Continued)

Primary Examiner — Timothy R Waggoner
(74) Attorney, Agent, or Firm — Socal IP Law Group LLP; Nikki M. Dossman

(57) ABSTRACT

Systems and methods for customizing beverage profiles, such as customizing beverage pods via input received via web-based portals or interfaces, are described. For example, the systems and methods may provide users with interactive interfaces that facilitate the reception of user input regarding the customization of a beverage, such as the customization of a nutritional or flavor profile of a beverage, such as a smoothie.

16 Claims, 12 Drawing Sheets

Related U.S. Application Data

(60) Provisional application No. 62/297,632, filed on Feb. 19, 2016, provisional application No. 62/297,644, filed on Feb. 19, 2016, provisional application No. 62/296,851, filed on Feb. 18, 2016, provisional application No. 62/297,716, filed on Feb. 19, 2016, provisional application No. 62/296,814, filed on Feb. 18, 2016, provisional application No. 62/296,844, filed on Feb. 18, 2016, provisional application No. 62/297,711, filed on Feb. 19, 2016, provisional application No. 62/297,009, filed on Feb. 18, 2016.

(51) Int. Cl.
| | |
|---|---|
| *B65D 51/28* | (2006.01) |
| *A47J 31/40* | (2006.01) |
| *A47J 31/00* | (2006.01) |
| *B65D 25/08* | (2006.01) |
| *A47J 31/52* | (2006.01) |
| *A23L 2/12* | (2006.01) |
| *A47J 31/44* | (2006.01) |
| *A61B 5/11* | (2006.01) |
| *A61B 5/16* | (2006.01) |
| *A63B 24/00* | (2006.01) |
| *B65D 85/804* | (2006.01) |
| *G06F 3/0482* | (2013.01) |
| *G06F 3/0484* | (2013.01) |

(52) U.S. Cl.
CPC ...... *G06F 3/04847* (2013.01); *A23V 2002/00* (2013.01); *A61B 2503/12* (2013.01); *A63B 2024/0065* (2013.01); *A63B 2024/0068* (2013.01)

(56) References Cited

U.S. PATENT DOCUMENTS

| | | | |
|---|---|---|---|
| 2005/0048461 A1* | 3/2005 | Lahteenmaki | A61J 3/002 435/3 |
| 2006/0081653 A1* | 4/2006 | Boland | A47J 31/40 222/243 |
| 2006/0271394 A1 | 11/2006 | Kelly | |
| 2008/0089983 A1* | 4/2008 | Coste | A23G 9/04 426/106 |
| 2009/0105875 A1* | 4/2009 | Wiles | G07F 9/026 700/239 |
| 2011/0289044 A1 | 11/2011 | Harrison | |
| 2012/0285986 A1* | 11/2012 | Irvin | B67D 1/0041 222/1 |
| 2014/0072679 A1 | 3/2014 | Balassanian | |
| 2015/0093725 A1 | 4/2015 | Baarman et al. | |
| 2015/0374025 A1* | 12/2015 | Evans | B65D 77/04 99/495 |
| 2016/0292391 A1* | 10/2016 | Fink | G06F 19/3475 |
| 2017/0039797 A1* | 2/2017 | Elmery | G07F 17/0071 |
| 2017/0358020 A1* | 12/2017 | Bender | G06Q 30/0621 |

OTHER PUBLICATIONS

Korean Intellectual Property Office, Written Opinion of the International Searching Authority for PCT Application No. PCT/US2017/018501, dated Apr. 26, 2017.

\* cited by examiner

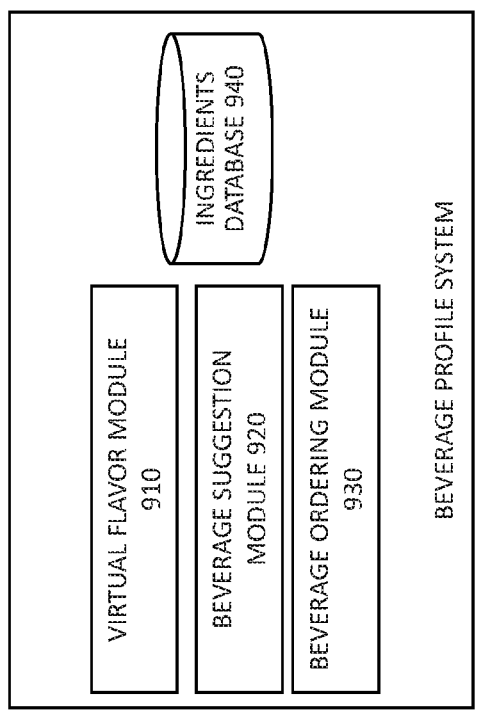
FIG. 9

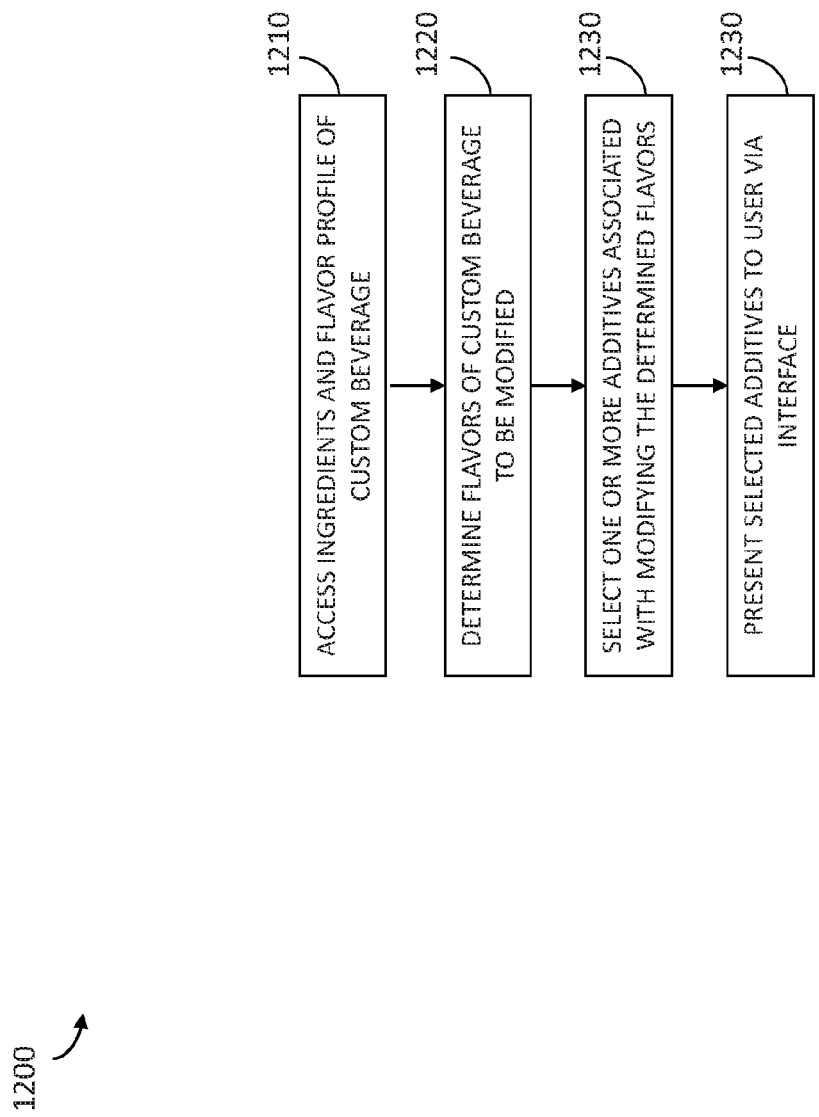

RECOMMENDING MODIFICATION FOR POD-BASED BEVERAGES

CROSS-REFERENCE TO RELATED APPLICATION(S)

This application is a bypass continuation of Patent Cooperation Treaty Application No.: PCT/US2017/018501, filed on Feb. 17, 2017, entitled "RECOMMENDING MODIFICATION FOR POD-BASED BEVERAGES", which claims priority to the following U.S. Provisional Patent Applications: U.S. Provisional Patent Application No. 62/296,814 filed on Feb. 18, 2016, entitled "PROVIDING A USER INTERFACE FOR CUSTOMIZING BEVERAGE PROFILES;" U.S. Provisional Patent Application No. 62/296, 844 filed on Feb. 18, 2016, entitled "REFRIGERATOR WITH POD-BASED BEVERAGE DISPENSER;" U.S. Provisional Patent Application No. 62/296,851 filed Feb. 18, 2016, entitled "CUSTOMIZING BEVERAGE PROFILES TO USER SLEEP CYCLES;" U.S. Provisional Patent Application No. 62/297,009 filed Feb. 18, 2016, entitled "RECOMMENDING MODIFICATIONS TO USER-CREATED BEVERAGE PROFILES;" U.S. Provisional Patent Application No. 62/297,644 filed Feb. 19, 2016, entitled "CUSTOMIZING BEVERAGE PROFILES TO USER MENTAL ACUITY;" U.S. Provisional Patent Application No. 62/297,711 filed Feb. 19, 2016, entitled "PORTABLE, POD-BASED SMOOTHIE MAKER;" U.S. Provisional Patent Application No. 62/297,716 filed Feb. 19, 2016, entitled "CUSTOMIZING BEVERAGE PROFILES TO USER WELLNESS PROGRAMS;" and U.S. Provisional Patent Application No. 62/297,632 filed Feb. 19, 2016, entitled "CUSTOMIZING BEVERAGE PROFILES TO USER ACTIVITIES;" each of which are hereby incorporated by reference in their entirety.

BACKGROUND

There are numerous retailers, distributors, and companies that attempt to target users with supplements, beverages, and other nutritional foods or drinks. However, most of these products are pre-made and generic to a certain population of users and/or for a certain purpose. For example, companies create sports drinks to assist the performance of a generic user during activities, and retailers sell smoothies that promote certain health benefits to a large population of users.

BRIEF DESCRIPTION OF THE DRAWINGS

Embodiments of the disclosed technology will be described and explained through the use of the accompanying drawings.

FIG. 9 is a block diagram illustrating components of a beverage profile system.

FIG. 12 is a flow diagram illustrating a method for modifying a flavor profile of a beverage for a user.

Figure 1:
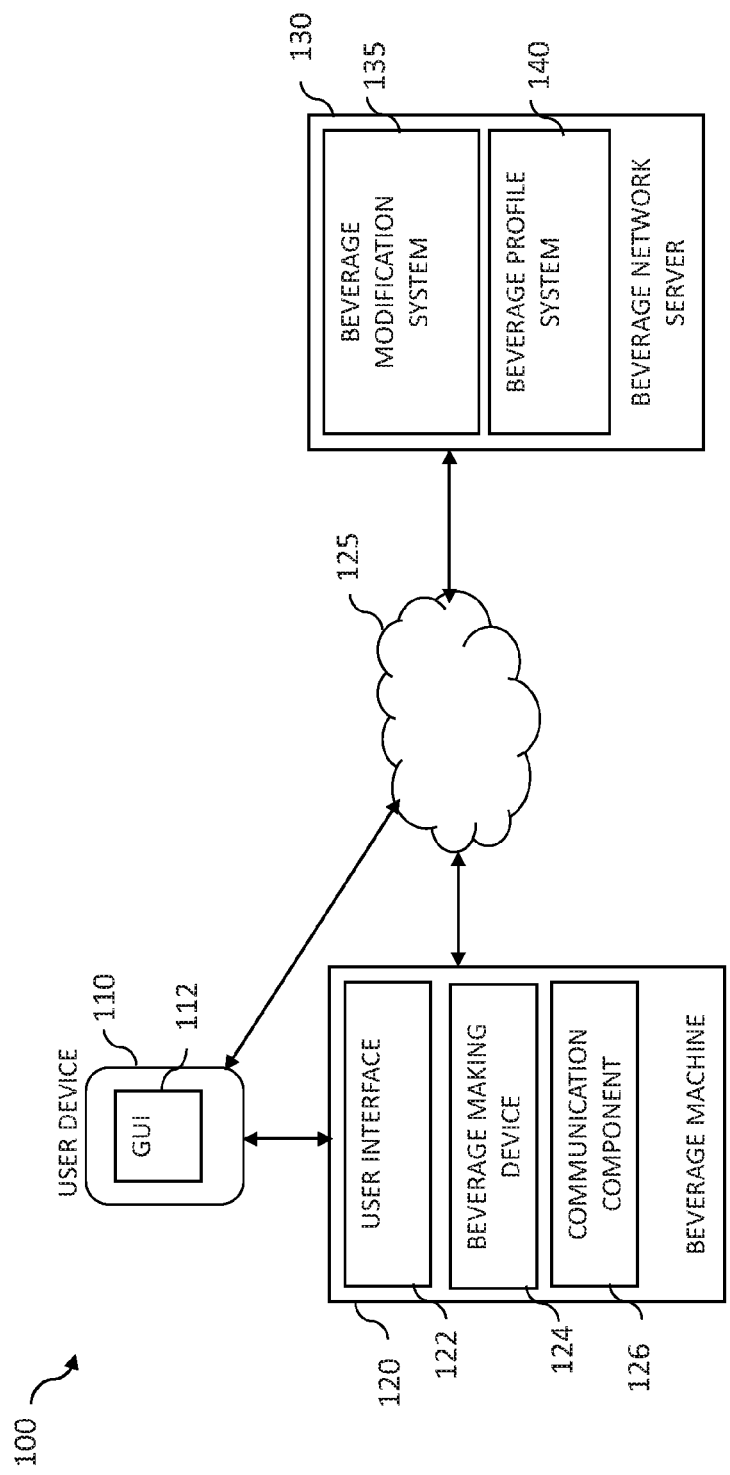
FIG. 1 is a block diagram illustrating a suitable computing environment 100 within which users may design and customize beverages.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Overview

Systems and methods for customizing beverage profiles, such as customizing smoothie pods via input received via web-based portals or interfaces, are described. For example, the systems and methods may provide users with interactive interfaces that facilitate the reception of user input regarding the customization of a beverage, such as the customization of a nutritional or flavor profile of a beverage.

The systems and methods may make beverages (e.g., smoothies or other drinks) and/or order or create smoothie pods (e.g., containers of ingredients used when making a beverage) having the customized beverage profiles. The systems and methods, therefore, may provide the user with a customized smoothie or other beverage that includes ingredients useful in improving, benefiting, or mitigating the user's health, performance, mental state, and/or other characteristics or states, among other benefits.

Suitable Computing Environment

As described herein, the systems and methods customize beverage profiles for users based on various aspects or characteristics associated with the users, and create or customize smoothie pods having ingredients that include the customized beverage profiles. FIG. 1 is a block diagram illustrating a suitable computing environment 100 for providing beverages having customized beverage profiles to a user.

The computing environment 100 includes a user device 110 (having a user interface 112). A beverage machine 120, such as a machine, device, or refrigerator configured to create beverages from pods or other ingredients sources, may be directly connected to the user device 110 or may communicate with the user device 110 or other devices, systems, and/or servers over a network 125, such as the Internet.

The beverage machine 120, therefore, may include a communication component 126 that facilitates communicating with various devices over the network 125, a user interface component 122 that renders, displays, and/or presents information to users via a display, such as a graphical user interface (GUI), and/or receives input from users via the display or via various manual controls of the beverage machine 120. The beverage machine 120 also includes a beverage making device 124, such as a blender or other pod-based beverage creating or making devices.

For example, the beverage making device 124 may be configured to extract contents (e.g., ingredients) within a beverage pod, such as a smoothie pod, and mix or combine the extracted contents with various liquids or other mixing substances, such as water, ice, milk, and so on, based on received or stored programs, recipes, and/or instructions. The beverage pods may be pods or cartridges containing specific mixtures of ingredients. For example, a pod may include a mixture of various freeze dried fruits (e.g., freeze dried bananas, strawberries, blueberries, mango, and so on), freeze dried vegetables (e.g., kale, spinach, beets, and so on), additive powders (e.g., protein powders, powdered greens), oils, seeds, supplements, flavors, and so on. In some cases, a pod may include a mixture of many different ingredients. In other cases, the pod may include one or more ingredients.

A beverage network server 130 may support and/or provide a "beverage network" or other cloud-based systems that perform various actions or functions to determine or create beverage profile recommendations for users. For example, the server 130, which may communicate with the beverage machine 120 or the user device 110 over the network 125, may include various different systems configured to access, receive, obtain, or retrieve certain information about or received from a user and generate beverage profiles for beverages targeted or customized for the user.

Example systems, which are discussed in greater detail herein, include a beverage modification system 135 that is configured to determine beverage modification recommendations to users based on requested nutritional profiles for the beverages, and a beverage profile system 140 that is configured to determine beverage modification recommendations to users based on requested flavor profiles for the beverages. The server 130 may also include other recommendation systems, such as those described in related PCT Application No. PCT/US17/18494, filed on Feb. 17, 2017, entitled CUSTOMIZING BEVERAGE PROFILES FOR A USER, which is incorporated by reference in its entirety.

Further details regarding the systems, devices, methods, and routines utilized to provide and/or implement various aspects of the computing environment 100 will be described herein. The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

FIG. 1 and the discussion herein provide a brief, general description of the suitable computing environment 100 in which the system can be supported and implemented. Although not required, aspects of the system are described in the general context of computer-executable instructions, such as routines executed by a general-purpose computer, e.g., mobile device, a server computer, or personal computer. Those skilled in the relevant art will appreciate that the system can be practiced with other communications, data processing, or computer system configurations, including: Internet appliances, hand-held devices (including tablet computers and/or personal digital assistants (PDAs)), all manner of cellular or mobile phones, multi-processor systems, microprocessor-based or programmable consumer electronics, set-top boxes, network PCs, mini-computers, mainframe computers, and the like. Indeed, the terms "computer," "host," and "host computer," and "mobile device" and "handset" are generally used interchangeably herein, and refer to any of the above devices and systems, as well as any data processor.

Aspects of the system can be embodied in a special purpose computing device or data processor that is specifically programmed, configured, or constructed to perform one or more of the computer-executable instructions explained in detail herein. Aspects of the system may also be practiced in distributed computing environments where tasks or modules are performed by remote processing devices, which are linked through a communications network, such as a Local Area Network (LAN), Wide Area Network (WAN), or the Internet. In a distributed computing environment, program modules may be located in both local and remote memory storage devices.

Aspects of the system may be stored or distributed on computer-readable media (e.g., physical and/or tangible non-transitory computer-readable storage media), including magnetically or optically readable computer discs, hard-wired or preprogrammed chips (e.g., EEPROM semiconductor chips), nanotechnology memory, or other data storage media. Indeed, computer implemented instructions, data structures, screen displays, and other data under aspects of the system may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the system reside on a server computer, while corresponding portions reside on a client computer such as a mobile or portable device, and thus, while certain hardware platforms are described herein, aspects of the system are equally applicable to nodes on a network. In an alternative embodiment, the mobile device or portable device may represent the server portion, while the server may represent the client portion.

Examples of Customizing Nutritional Profiles of Beverages for Users

As described herein, in some embodiments, the systems and methods provide an interactive, web-based portal, interface (e.g., graphical user interface, or GUI), and/or platform for designing and creating smoothie pods and other beverage pods. Via the interface, the systems facilitate the reception of user input regarding various ingredients and substances, and associated amounts, percentages, or levels (e.g., levels of freeze dried fruit, supplements, and so on) to be added when customizing smoothie pods for users.

For example, the interface enables a user to add a level of freeze dried fruit, supplements, and so on (e.g., ingredients for a smoothie pod). The web portal displays the associated health benefits and supplements (e.g., protein, vitamins, and so on) that result, as the ingredients are added. The displayed information enables the user to see the effect of adding supplements to a smoothie pod, and facilitates a user adjusting different aspects of a smoothie for their health and wellness, among other benefits.

Further, the systems may suggest supplements based upon proposed diet, disease state, training regime, and so on, of the user. For example, when the user enters what ingredients/supplements they plan on using, the system recommends an amount of each supplement that can be added without distorting the taste. Thus, the web portal may depict a flavor type and level as ingredients are added, providing users with a visual representation or depiction of the smoothie pod, and the effect of adding items to the customized smoothie pod.

Therefore, the systems described herein may provide various users (e.g., users concerned with nutrition and contents of pre-made pods, users with sensitive pallets or picky flavor preferences, users with special needs/allergies, users with children, and so on), with the ability to control and make customized smoothie pods, utilizing presented interfaces to assist the users with creating their smoothie pods, tuning the flavoring of the smoothie pods, and so on.

As described herein, the user, via the custom beverage GUI of the user device 110 or machine 120, selects parameters for a customized beverage, and the device 110 or machine 120 transfers the parameters to the beverage modification system 135 of the beverage network server 130.

Figure 2:
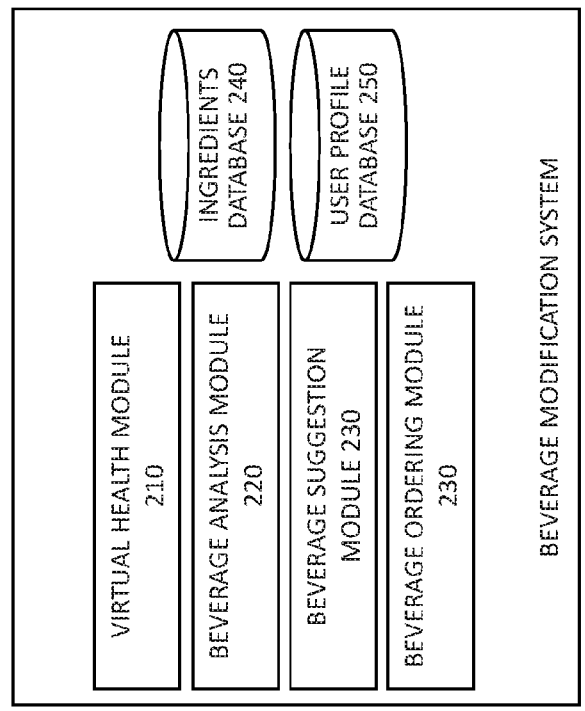
FIG. 2 is a block diagram illustrating components of a beverage modification system.

FIG. 2 is a block diagram illustrating components of the beverage modification system 135. For example, the beverage modification system 135 includes a virtual health module 210 that analyzes the parameters and compares the parameters to information stored in an ingredients database 240, which stores data structures that relate ingredients to their nutritional profiles (e.g., vitamins, calories, and so on).

A beverage analysis module 220 may determine, using the comparison of parameters to information in the ingredients database 240, a beverage or nutritional profile for the user customized beverage. A health or user profile database 250 contains data about the nutritional value and health effects of ingredients and/or health information for the user, and provides the system 135 with information associated with the nutritional value and health effects of a beverage, such as the customized beverage.

A beverage suggestion module 230 generates a suggestion or recommendation associated with modifying, adjusting, and/or improving the nutritional profile (or, flavor or other aspects) of the beverage. For example, the beverage suggestion module 230 may identify one or more ingredients, additives, or supplements to add to the customized beverage to reduce or compensate for differences between user goals and the profile of the customized beverage.

Further, the system 135 may include a beverage ordering module 230 that enables the user to order a beverage pod (e.g., smoothie pod) that, when placed in the beverage machine 120, produces the customized beverage (e.g., smoothie) designed by the user (and, optionally, based on suggestions by the system).

Figure 3C:
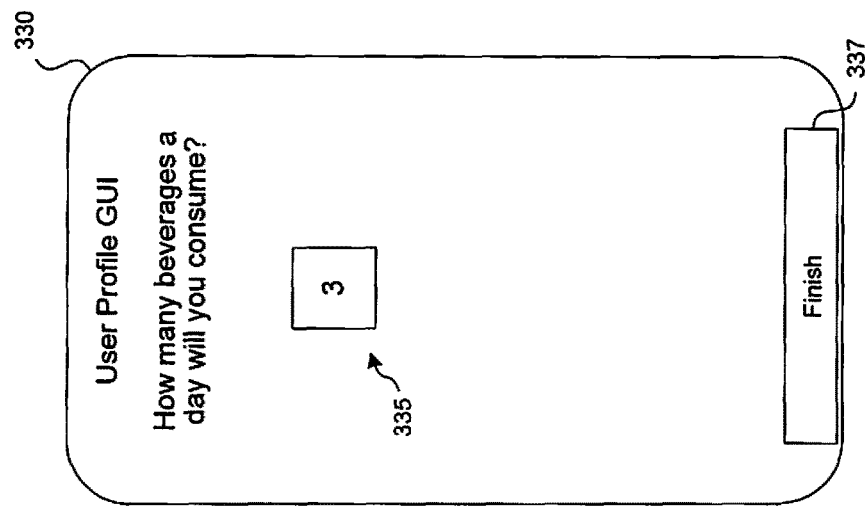
FIGS. 3A-3C are display diagrams illustrating user interfaces for receiving user information.
Figure 3B:
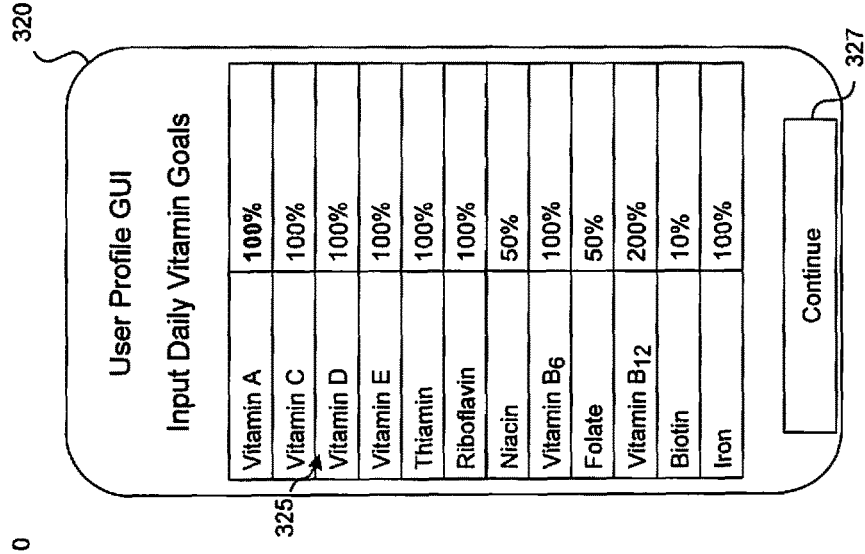
Figure 3A:
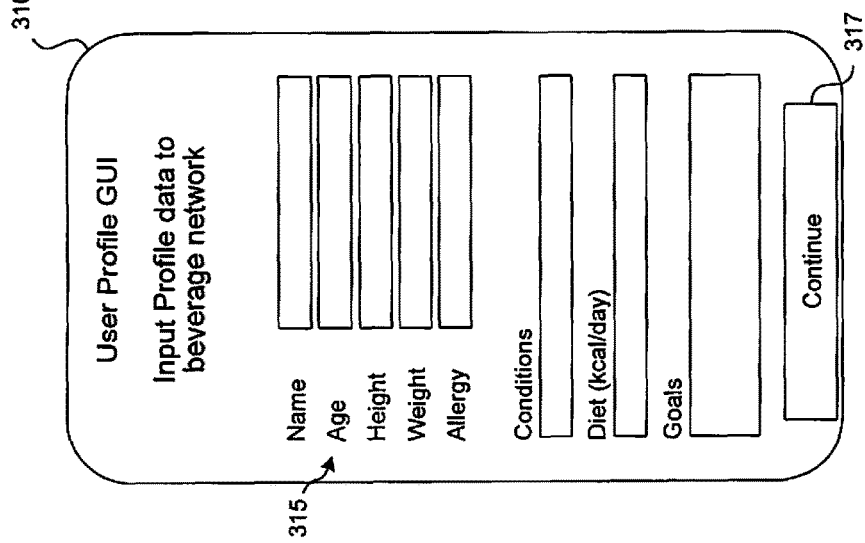

As described herein, the systems and methods facilitate the customization of beverages for users via various displayed user interfaces. FIGS. 3A-3C are display diagrams illustrating user interfaces for receiving user information.

As shown in FIG. 3A, a user interface 310 facilitates the input of user information 315, such as biographical information, health information, demographic information, vital information, and so on. Once input, the user may select an option 317 to continue, and the system presents a user interface 320, as shown in FIG. 3B.

User interface 320 presents vitamin goal information, and facilitates receiving user input regarding the goal information. For example, the interface 320 may receive input that identifies daily percentage goals for different vitamins 325, caloric intake goals, and so on. Once the goals are provided, the user may select an option 327 to continue, and the system presents a user interface 330, as shown in FIG. 3C.

The user interface 330 includes elements that facilitate receiving input that identifies consumption parameters or goals 335 for the user. For example, the user may provide a number of beverages to be prepared and consumed each day by the user, a total amount of beverages to be consumed, a percentage of total calories to be allotted to the beverages, and so on. Once the information is input, the user may select a finish option 337, which causes the system to analyze the information provided by the user and display information associated with the beverage being customized by the user.

Figure 4:
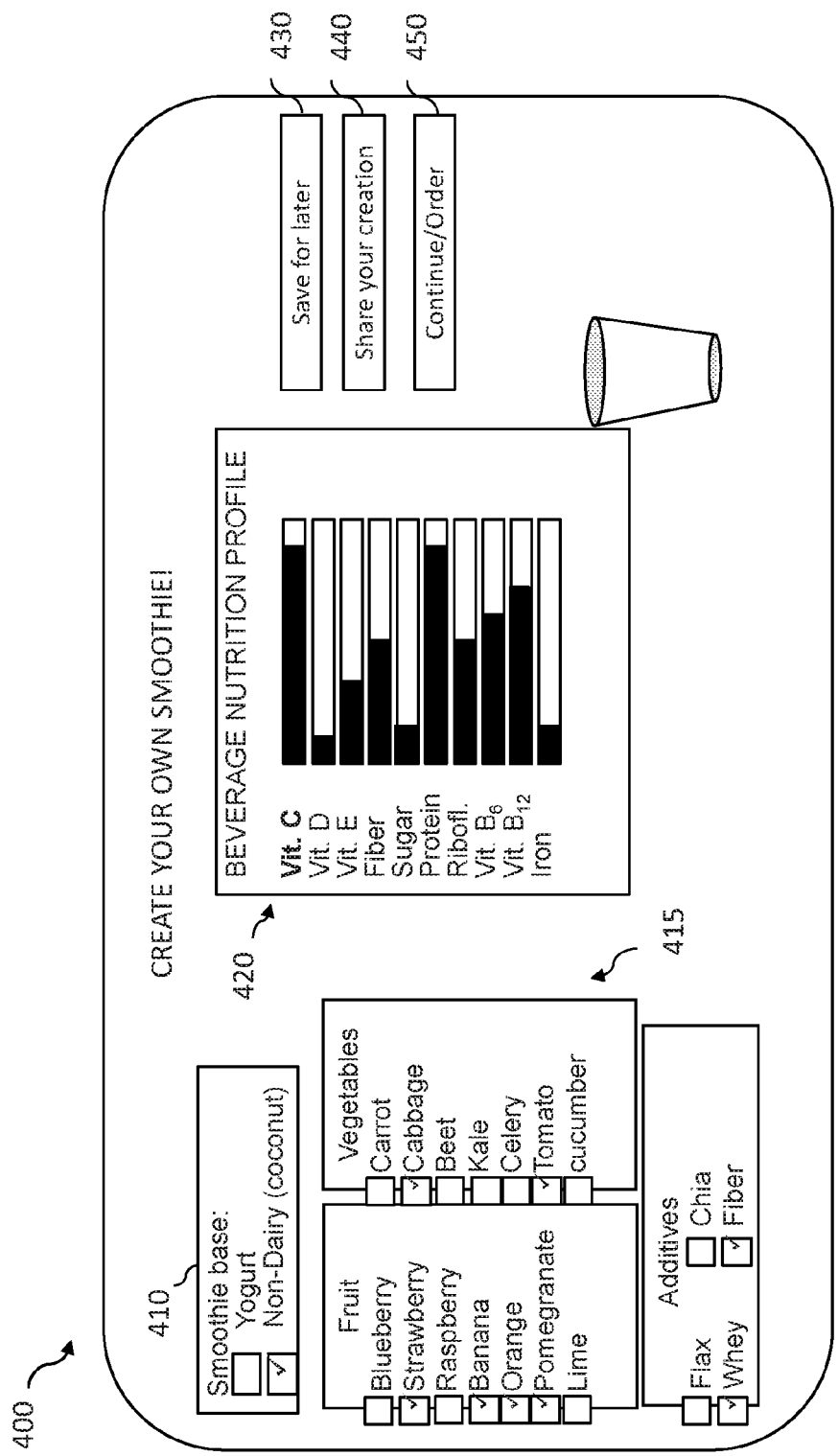
FIG. 4 is display diagram illustrating a user interface for receiving input about a beverage and displaying a nutritional profile for the beverage.

FIG. 4 is display diagram illustrating a user interface 400 for receiving input about a beverage and displaying a nutritional profile for the beverage. The interface 400 enables the user to select a base 410 for the beverage and one or more ingredients or additives 415 that they would like to be included in their beverage. The interface then presents an expected nutritional profile 420 for the beverage based on the user's received customization input. The user may then select one or more actions to be performed, such as an option 430 to save the created beverage, an option 440 to share information about the beverage with others (e.g., via their social networks), an option 450 to continue, order, or make the beverage, and so on.

Figure 5:
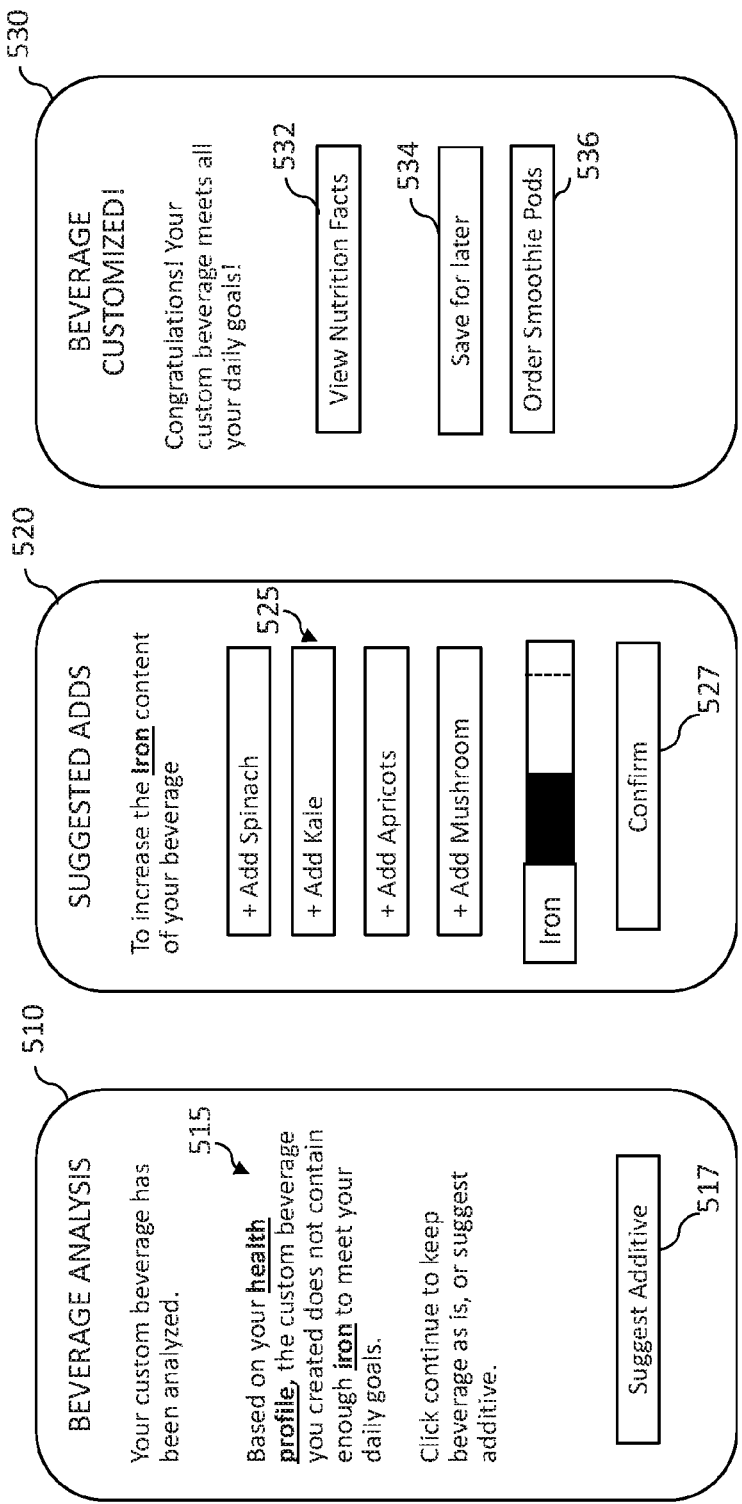
FIGS. 5A-5C are display diagrams illustrating user interfaces for customizing a beverage for a user.

FIGS. 5A-5C are display diagrams illustrating user interfaces for customizing a beverage for a user. As shown in user interface 510 of FIG. 5A, the system 135 compares the user's health or nutritional goals with the determined nutritional profile of the customized beverage (see FIG. 4), and presents information 515 that indicates a result of the comparison. For example, as depicted, the system 135 determined that the user's customized beverage does not include a sufficient amount of iron to meet the user's goal, and presents an option 517 to facilitate a suggestion of an additive to the customized beverage.

When the user selects the option 517 to present a suggestion of an additive, the system 135 causes user interface 520, as shown in FIG. 5B, to be displayed. User interface 520 presents various suggested additives, which, if added to the customized beverage, will add or compensate for the determined nutritional deficiency (e.g., low iron) of the customize beverage. For example, the interface 520 displays various additive options 525 that, when selected by the user and requested 527 to be added, modify the nutritional profile of the customized beverage.

FIG. 5C presents a user interface 530 that presents results of modifying the customized beverage and information associated with the beverage. For example, the interface 530 includes options to view the updated nutritional profile 532 for the beverage, save the beverage 534 for later, order the beverage 536, make the beverage (if available), and so on.

Therefore, in some embodiments, the beverage modification system 135 provides various user interfaces to receive input from users, display beverage and/or nutritional profiles for customized beverages, present recommended ingredients or additives, order or make the beverages, and other information or options to be acted upon by users when customizing and obtaining smoothies and other beverages for consumption.

Figure 6:
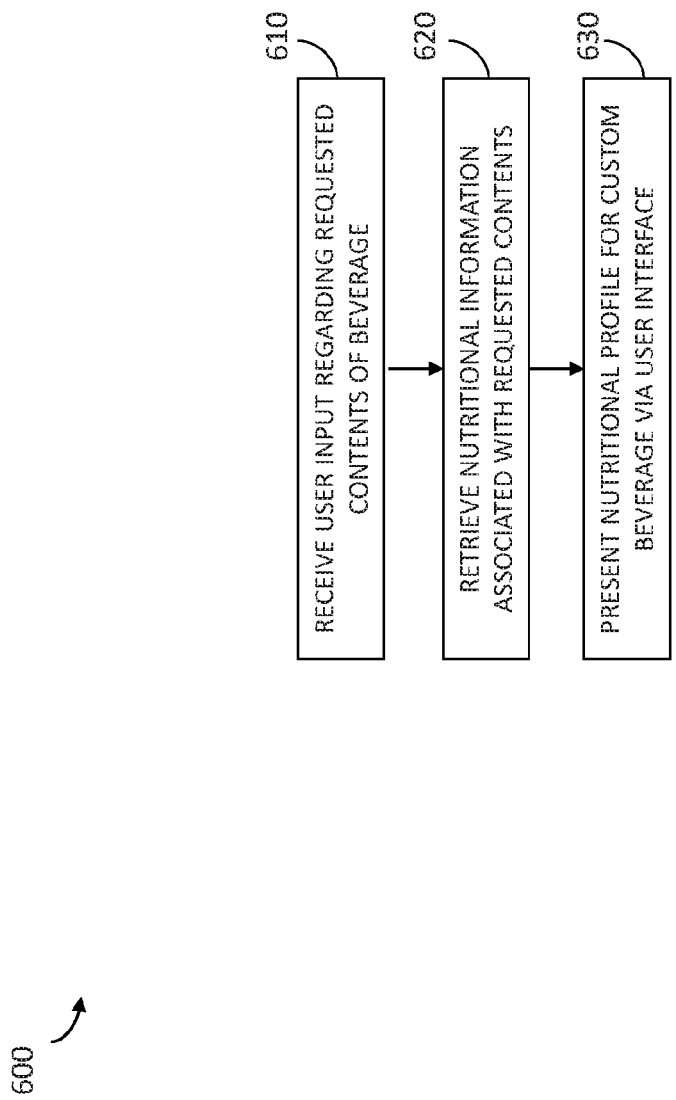
FIG. 6 is a flow diagram illustrating a method for determining a nutritional profile for a customized beverage.

As described herein, the system 135 may perform various processes, operations, or methods when determining profile information for beverages and/or recommending beverages or ingredients to users. FIG. 6 is a flow diagram illustrating a method 600 for determining a nutritional profile for a customized beverage. Aspects of the method 600 may be performed by the beverage modification system 135 and, accordingly, is described herein merely by way of reference thereto. It will be appreciated that the method 600 may be performed on any suitable hardware.

As depicted, the method 600 may perform operations to determine nutritional information for a user-created beverage. For example, in operation 610, the system 135 receives user input regarding requested contents of a beverage. In operation 620, the system 135 retrieves nutritional information (e.g., beverage profiles or nutritional profiles) associated with the request contents. In operation 630, the system 135, via one or more interfaces, presents (or causes to present) a nutritional profile (see FIG. 4) for the custom beverage.

Figure 7:
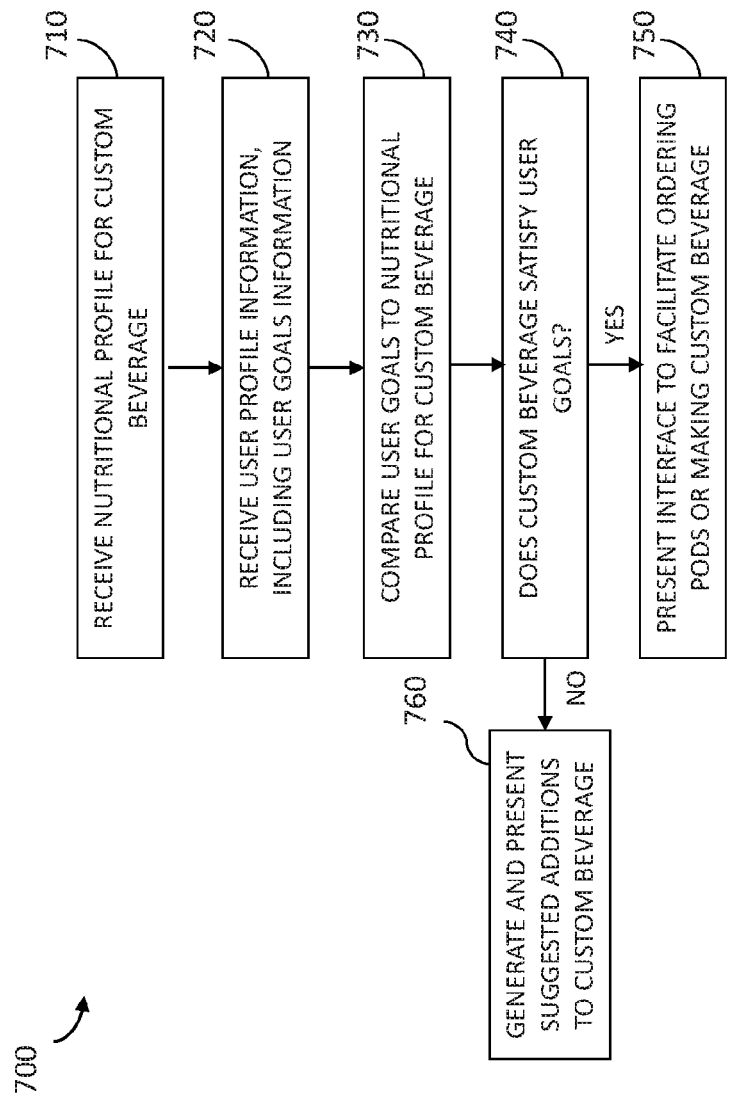
FIG. 7 is a flow diagram illustrating a method for customizing a beverage for a user.

FIG. 7 is a flow diagram illustrating a method 700 for customizing a beverage for a user. Aspects of the method 700 may be performed by the beverage modification system 135 and, accordingly, is described herein merely by way of reference thereto. It will be appreciated that the method 700 may be performed on any suitable hardware.

As depicted, the method 700 may perform operations to determine whether a user-created beverage satisfies the user-provided nutritional goals. For example, in operation 710, the system 135 receives or accesses a nutritional profile for a customized beverage, and in operation 720, receives or accesses user profile information, such as user goal information.

In operation 730, the system 135 compares the user goal information to the nutritional profile for the customized beverage. When the customized beverage has a nutritional profile that matches the user's goals, the method 700 proceeds to operation 750, and the system 135 presents an interface to order one or more pods containing ingredients for the customize beverage (or, to make the beverage). When the customized beverage does not have a nutritional profile that matches the user's goals (e.g., is lacking one or more vitamins), the method 700 proceeds to operation 760, and the system 135 determines, generates, and/or presents suggested additives or ingredients to add to the customized beverage (see FIG. 5B).

Figure 8:
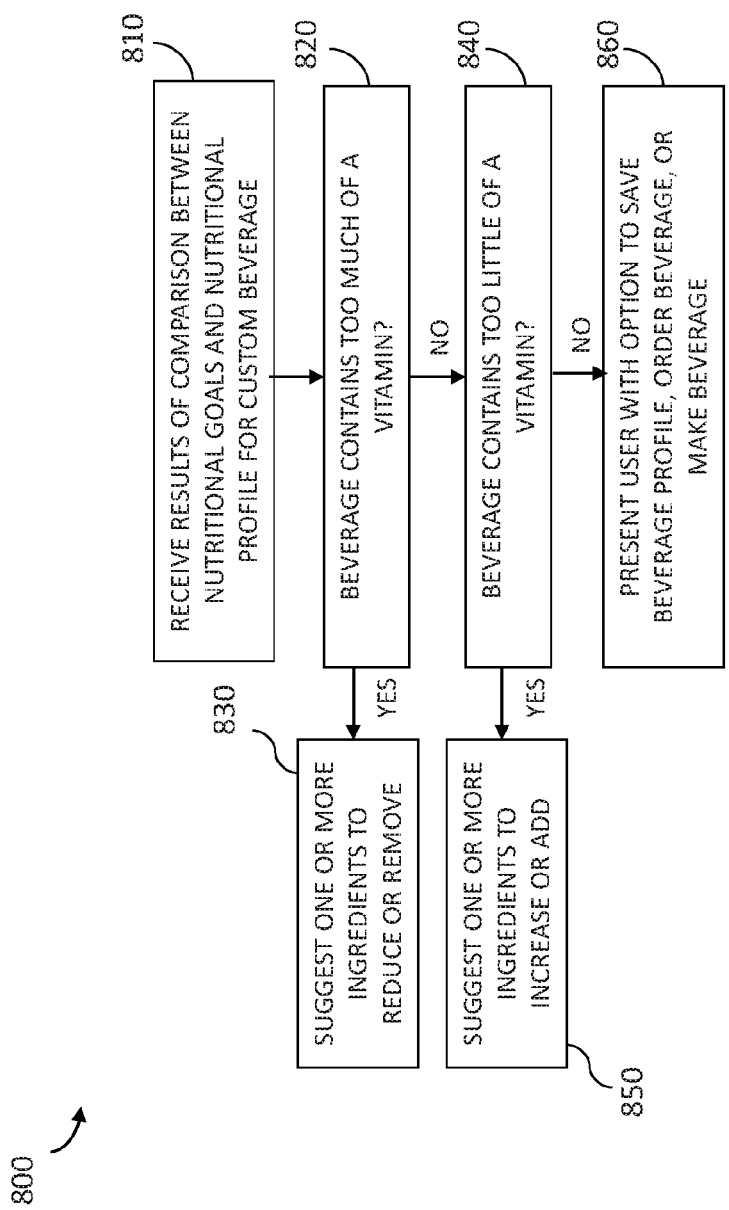
FIG. 8 is a flow diagram illustrating a method for modifying a nutritional profile of a beverage for a user.

FIG. 8 is a flow diagram illustrating a method 800 for modifying a nutritional profile of a beverage for a user. Aspects of the method 800 may be performed by the beverage modification system 135 and, accordingly, is described herein merely by way of reference thereto. It will be appreciated that the method 800 may be performed on any suitable hardware.

As depicted, the method 800 may perform operations to provide suggestions to modify the user-created beverage. For example, in operation 810, the system 135 receives results of a comparison between user nutritional goals and a nutritional profile for a customized beverage.

In operation 820, the system 135 determines whether the nutritional profile includes too much of a vitamin. When the nutritional profile includes too much of a vitamin, the method 800 proceeds to operation 830, and the system 135 presents suggestions of one or more ingredients to reduce or remove from the customized beverage.

When the nutritional profile does not include too much of a vitamin, the method 800 proceeds to operation 840, and the system 135 determines whether the nutritional profile contains too little of a vitamin. When the nutritional profile includes too little of a vitamin, the method 800 proceeds to operation 850, and the system 135 presents suggestions of one or more ingredients to increase or add to the customized beverage. When the nutritional profile does not include too little of a vitamin, the method 800 proceeds to operation 860, and presents the user with options to save the beverage, order pods for the beverage, make the beverage, and so on (see FIG. 5C).

Thus, in some embodiments, the beverage modification system 135 may perform a method for designing a smoothie pod or other beverage pod by receiving input from a user via a user device that communicates with the system 135 over a network, where the input is received via a graphical user interface and includes selections of ingredients to be added to the smoothie pod, determining a nutritional profile for the smoothie pod, identifying a nutritional goal for the user, and presenting a suggestion via the graphical user interface of one or more additional ingredients to be added to the smoothie pod to modify the nutritional profile of the smoothie pod based on the nutritional goal for the user.

Examples of Customizing Flavor Profiles of Beverages for Users

As described herein, in some embodiments, the systems and methods provide an interactive, web-based portal, interface (e.g., graphical user interface, or GUI), and/or platform for designing and creating smoothie pods and other beverage pods. Via the interface, the systems facilitate the reception of user input regarding various ingredients and substances, and associated amounts or levels (e.g., levels of freeze dried fruit, supplements, and so on) to be added when customizing smoothie pods for users.

For example, the web portal may depict a flavor type and level as ingredients are added, providing users with a visual representation or depiction of the smoothie pod, and the effect of adding items (e.g., flavoring additives or ingredients) to the customized smoothie pod. The systems and methods determine flavoring to be added to smoothie pods, such as when the flavor is degraded (or, predicted to be degraded) when too many supplements (or incongruous mixtures) are added to the pods. Further, the systems may determine various flavoring adjustments or modifications, and provide suggestions to users during the creation of the smoothie pods.

Therefore, the systems described herein may provide various users (e.g., users concerned with nutrition and contents of pre-made pods, users with sensitive pallets or picky flavor preferences, users with special needs/allergies, users with children, and so on), with the ability to control and make customized smoothie pods, utilizing presented interfaces to assist the users with creating their smoothie pods, tuning the flavoring of the smoothie pods, and so on.

FIG. 9 is a block diagram illustrating components of the beverage profile system 140. The beverage profile system 140 includes a virtual flavor module 910 that analyzes parameters of a user customized beverage, using data from an ingredients database 940 that is associated with the beverage profile system 140. For example, the virtual flavor module may determine or identify at least one of many flavor profiles: bitter, sweet, sour, savory, salty, anise, and so on, as well as determine whether a flavor profile for the beverage is acceptable or palatable to the user.

Table 1 illustrates example data stored by the ingredients database.

TABLE 1

| Ingredient | Type | Bitter | Sweet | Salty | Savory | Sour | Add to: |
|---|---|---|---|---|---|---|---|
| Banana | Fruit | 0% | 20% | 0% | 5% | 5% | Sour |
| Kale | Veg | 30% | 0% | 5% | 10% | 0% | Sweet |
| Whey | Additive | 10% | 10% | 5% | 20% | 0% | Salty |
| Honey | Additive | 5% | 50% | 0% | 5% | 10% | Bitter |

TABLE 1-continued

| Ingredient | Type | Bitter | Sweet | Salty | Savory | Sour | Add to: |
|---|---|---|---|---|---|---|---|
| Durian | Fruit | 50% | 10% | 5% | 10% | 10% | Sweet |
| Beet | Veg | 20% | 5% | 40% | 15% | 5% | Sweet |

For example, if the virtual flavor module 910 determines a customized beverage is too sour, it may identify a banana as a recommended ingredient to add to the beverage, using the data of Table 1 that is stored in the ingredients database 940.

The beverage profile system 140 also includes a beverage suggestion module 920 that generates a suggestion or recommendation associated with modifying, adjusting, and/or improving the flavor of the beverage. For example, the module 920 may recommend adding a certain percentage of banana to a beverage having a flavor profile that indicates a sour flavor type is above a certain acceptable percentage of the overall flavor profile.

Further, the system 140 may include a beverage ordering module 930 that enables the user to order a beverage pod (e.g., smoothie pod) that, when placed in the beverage machine 120, produces the customized beverage (e.g., smoothie) designed by the user (and, optionally, based on suggestions by the system).

As described herein, the systems and methods facilitate the customization of beverages for users via various displayed user interfaces.

Figure 10:
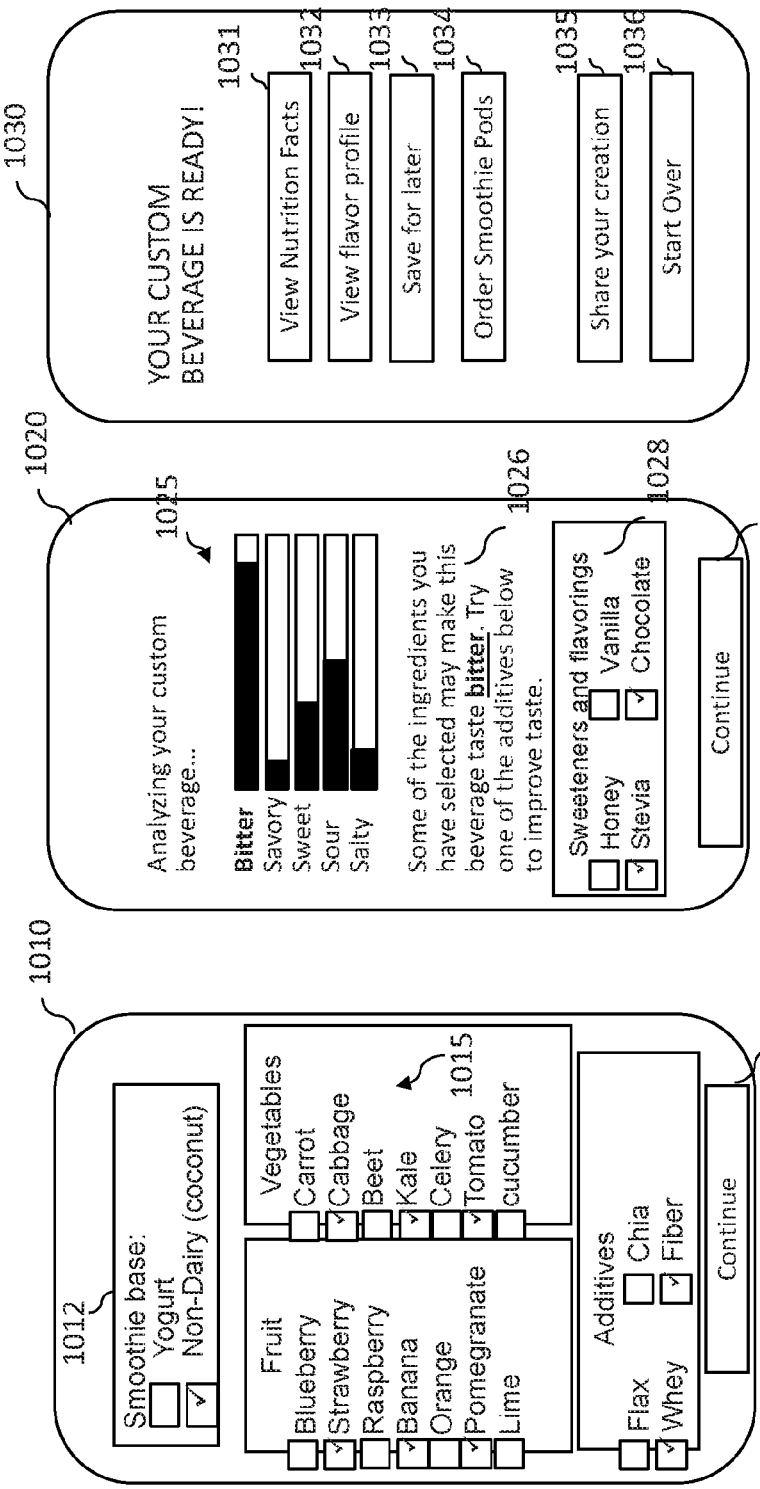
FIGS. 10A-10C are display diagrams illustrating user interfaces that facilitate modifying a flavor profile of a beverage for a user.

FIGS. 10A-10C are display diagrams illustrating user interfaces that facilitate modifying a flavor profile of a beverage for a user. FIG. 10A presents a user interface 1010 that enables the user to select a base 1012 for the beverage and one or more ingredients or additives 1015 that they would like to be included in their beverage.

Once the user selects an option 1017 to continue, the system 140, via an interface 1020 shown in FIG. 10B, presents an expected flavor profile 1025 for the beverage based on the user's received customization input, information 1026 suggesting an expected flavor for the beverage, and user-selectable options 1028 to add ingredients or additives (e.g., sweeteners, flavoring, and so on) to the beverage.

Once the user selects an option 1027 to continue, the system 140, via an interface 1030, shown in FIG. 10C, presents one or more actions to be performed, such as an option 1031 to view nutritional information for the beverage, an option 1032 to view a modified flavor profile, an option 1033 to save the created beverage, an option 1035 to share information about the beverage with others (e.g., via their social networks), an option 1034 to continue, order, or make the beverage, an option 1036 to create a new customized beverage, and so on.

Therefore, in some embodiments, the beverage profile system 140 provides various user interfaces to receive input from users, display beverage and/or flavor profiles for customized beverages, present recommended ingredients or additives, order or make the beverages, and other information or options to be acted upon by users when customizing and obtaining smoothies and other beverages for consumption.

Figure 11:
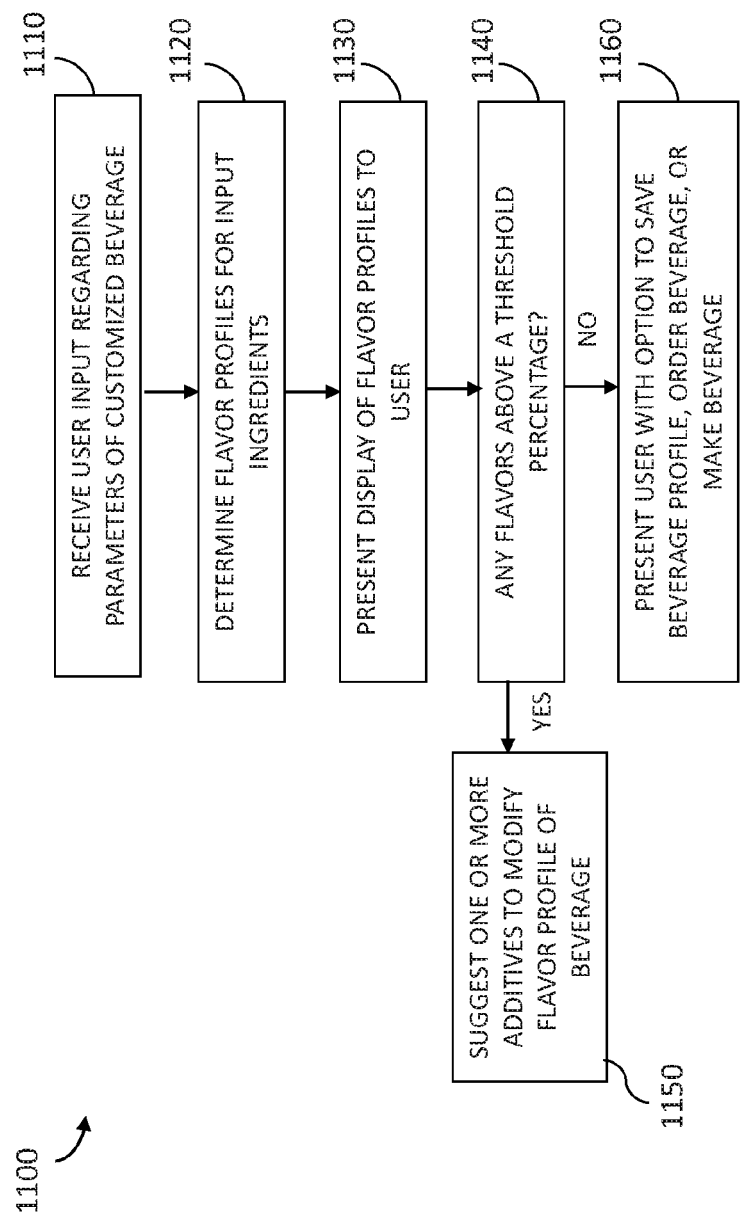
FIG. 11 is a flow diagram illustrating a method for customizing a beverage for a user.

As described herein, the system 140 may perform various processes, operations, or methods when determining flavor profile information for beverages and/or recommending beverages or ingredients to users. FIG. 11 is a flow diagram illustrating a method 1100 for customizing a beverage for a user. Aspects of the method 1100 may be performed by the beverage profile system 140 and, accordingly, is described herein merely by way of reference thereto. It will be appreciated that the method 1100 may be performed on any suitable hardware.

As depicted, the method 1100 may perform operations to create a beverage and/or determine modifications to adjust the flavor of a beverage. For example, in operation 1110, the system 140 receives user input regarding parameters of a customized beverage (see FIG. 10A), and in operation 1120, determines a flavor profile for the input ingredients.

In operation 1130, the system 140 presents, or causes to present, the flavor profiles to the user. In operation 1140, the system 1140 determines whether any flavor types are above a threshold percentage. When there is a flavor type above a threshold percentage, the method 1100 proceeds to operation 1150, and the system 140 suggests one or more additives to add to the beverage to modify the flavor profile of the beverage (see FIG. 10B).

When there is no flavor type above a threshold percentage, the method 1100 proceeds to operation 1160, and the system 140 presents the user options to perform one or more actions with respect to the beverage (see FIG. 10O), such as save the customized beverage, order smoothie pods associated with the beverage, make the beverage (e.g., using machine 120), and so on.

FIG. 12 is a flow diagram illustrating a method 1200 for modifying a flavor profile of a beverage for a user. Aspects of the method 1200 may be performed by the beverage profile system 140 and, accordingly, is described herein merely by way of reference thereto. It will be appreciated that the method 1200 may be performed on any suitable hardware.

As depicted, the method 1200 may perform operations to determine and recommend additives and other flavored substances used to adjust the flavor of a beverage. For example, in operation 1210, the system 140 accesses the ingredients and/or flavor profile for a customized beverage, and in operation 1220, determines flavors of the beverage to be modified.

In operation 1230, the system 140 selects or identifies one or more additives associated with modifying the determined flavor of the beverage (see Table 1), and in operation 1240, the system 140 presents the selected additives to the user via the user interface of the user device 110 or machine 120 (see FIG. 10B).

For example, the method 1200 may determine that a flavor profile of the smoothie pod that is based on the ingredients selected by the user includes at least one flavor type having a percentage of the flavor profile that is outside of an acceptable threshold percentage range of the flavor profile (e.g., above 60 percent of the flavor profile), and present a suggestion via the graphical user interface of one or more additional ingredients to be added to the smoothie pod to modify the percentage of the flavor type to be within the acceptable threshold percentage range (e.g., lower than 60 percent) of the flavor profile.

As another example, the method 1200 may determine a customized beverage has a flavor profile of "bitter" or "sweet" or another single type of flavor, and present recommendations based on the determined single flavor profile for the beverage.

Thus, in some embodiments, the system 140 may perform a method for designing a smoothie pod or other beverage by receiving input from a user via the user device 110 that communicates with the system 140 over a network, wherein the input is received via a graphical user interface and includes selections of ingredients to be added to the smoothie pod, determining, that a flavor profile of the smoothie pod that is based on the ingredients selected by the user includes at least one flavor type having a percentage of the flavor profile that is outside of an acceptable threshold percentage range of the flavor profile, and presenting a suggestion via the graphical user interface of one or more additional ingredients to be added to the smoothie pod to modify the percentage of the flavor type to be within the acceptable threshold percentage range of the flavor profile.

Examples of Ordering Beverage Pods

As described herein, in some embodiments, the systems and methods perform operations to generate and/or order customized beverages (e.g., smoothies) for users. For example, an ordering system (e.g., module 230 or 930) may perform the following steps when ordering beverage pods for use in the beverage machine 120:

Calculate a cost of ingredients and manufacturing for a smallest possible batch of pods (e.g., 5 ingredients at $0.25 each times 50 pods);

Calculate a sales margin based on retailer/manufacturer limits (e.g., 20% of manufacturing cost);

Calculate a cost outlay for different batch sizes (e.g., 50 pods=100%, 100 pods=99%, 500 pods=80%, and so on);

Present the calculated cost outlays to the users, which select a quantity based on the estimated costs; and Complete an order that considers the number of ingredients, sales margin, cost outlay, and/or other factors.

Therefore, in some embodiments, the systems and methods described here customize smoothie pods for users as well as customize quantities of smoothie pods to be ordered on behalf of users, among other benefits.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

We claim:

1. A method for designing a smoothie pod, the method comprising:
   receiving input from a user via a user device, wherein the input is received via a graphical user interface and includes selections of a smoothie base, food ingredients, and additives to be added to the smoothie pod;
   determining a nutritional profile for the smoothie pod based on the user selections of the smoothie base, food ingredients and additives;
   displaying the nutritional profile for the smoothie pod via the graphical user interface;
   identifying a nutritional goal for the user; and
   presenting a suggestion via the graphical user interface of one or more additional food ingredients or additives for selection by the user to be added to the smoothie pod to modify the nutritional profile of the smoothie pod based on the nutritional goal for the user.

2. The method of claim 1, wherein the graphical user interface is a graphical user interface of the user device.

3. The method of claim 1, wherein presenting a suggestion to modify the nutritional profile of the smoothie pod based on the nutritional goal for the user includes presenting information that displays the modified nutritional profile via the graphical user interface.

4. The method of claim 1, wherein identifying a nutritional goal for the user includes receiving input from the user via the graphical user interface that identifies a number of calories to be consumed by the user in a given day and one or more vitamin goals for the given day.

5. The method of claim 1, wherein identifying a nutritional goal for the user includes receiving input from the user via the graphical user interface that identifies a number of beverages to be consumed by the user in a given day.

6. The method of claim 1, wherein determining a nutritional profile for the smoothie pod includes determining a beverage profile for the smoothie pod based on the selections of ingredients to be added to the smoothie pod.

7. The method of claim 1, wherein presenting a suggestion via the graphical user interface of one or more additional food ingredients or additives for selection by the user to be added to the smoothie pod to modify the nutritional profile of the smoothie pod based on the nutritional goal for the user includes:
  determining differences between the nutritional profile of the smoothie pod and the nutritional goal for the user;
  identifying additional ingredients or additives that include vitamins to compensate for the determined differences; and
  displaying the additional food ingredients or additives for selection by the user.

8. The method of claim 1, further comprising:
  receiving a selection of the suggested one or more additional food ingredients or additives; and
  receiving an order selection from the user to order the smoothie pod based on the smoothie base, food ingredient, and additive selections and the additional food ingredients or additives selections.

9. A non-transitory computer-readable medium whose contents, when executed by a computing system, cause the computing system to perform a method for designing a smoothie pod, the method comprising:
  receiving input from a user via a user device, wherein the input is received via a graphical user interface and includes selections of a smoothie base, food ingredients, and additives to be added to the smoothie pod;
  determining a nutritional profile for the smoothie pod based on the user selections of smoothie base, food ingredients, and additives;
  displaying the nutritional profile for the smoothie pod via the graphical user interface;
  identifying a nutritional goal for the user; and
  presenting a suggestion via the graphical user interface of one or more additional food ingredients or additives for selection by the user to be added to the smoothie pod to modify the nutritional profile of the smoothie pod based on the nutritional goal for the user.

10. The non-transitory computer-readable medium of claim 9, wherein the graphical user interface is a graphical user interface of the user device.

11. The non-transitory computer-readable medium of claim 9, wherein presenting a suggestion to modify the nutritional profile of the smoothie pod based on the nutritional goal for the user includes presenting information that displays the modified nutritional profile via the graphical user interface.

12. The non-transitory computer-readable medium of claim 9, wherein identifying a nutritional goal for the user includes receiving input from the user via the graphical user interface that identifies a number of calories to be consumed by the user in a given day and one or more vitamin goals for the given day.

13. The non-transitory computer-readable medium of claim 9, wherein identifying a nutritional goal for the user includes receiving input from the user via the graphical user interface that identifies a number of beverages to be consumed by the user in a given day.

14. The non-transitory computer-readable medium of claim 9, wherein determining a nutritional profile for the smoothie pod includes determining a beverage profile for the smoothie pod based on the selections of ingredients to be added to the smoothie pod.

15. The non-transitory computer-readable medium of claim 9, wherein presenting a suggestion via the graphical user interface of one or more additional food ingredients or additives for selection by the user to be added to the smoothie pod to modify the nutritional profile of the smoothie pod based on the nutritional goal for the user includes:
  determining differences between the nutritional profile of the smoothie pod and the nutritional goal for the user;
  identifying additional food ingredients or additives that include vitamins to compensate for the determined differences; and
  displaying the additional food ingredients or additives for selection by the user.

16. The non-transitory computer-readable medium of claim 9, wherein the method further comprises:
  receiving a selection of the suggested one or more additional food ingredients or additives; and
  receiving an order selection from the user to order the smoothie pod based on the smoothie base, food ingredient, and additive selections and the additional food ingredients or additives selections.

* * * * *